US007137712B2

(12) United States Patent
Brunner et al.

(10) Patent No.: US 7,137,712 B2
(45) Date of Patent: Nov. 21, 2006

(54) REFLECTOR SYSTEM FOR DETERMINING POSITION

(75) Inventors: Georg Brunner, Constance (DE); Manfred Schmid, Herdwangen (DE)

(73) Assignee: Northern Digital Inc., Waterloo (CA)

( * ) Notice: Subject to any disclaimer, the term of this patent is extended or adjusted under 35 U.S.C. 154(b) by 224 days.

(21) Appl. No.: 10/168,381

(22) PCT Filed: Dec. 18, 2000

(86) PCT No.: PCT/EP00/12892

§ 371 (c)(1),
(2), (4) Date: Nov. 13, 2002

(87) PCT Pub. No.: WO01/47427

PCT Pub. Date: Jul. 5, 2001

(65) Prior Publication Data

US 2003/0174401 A1 Sep. 18, 2003

(30) Foreign Application Priority Data

Dec. 23, 1999 (DE) ............................. 199 62 376
Jun. 15, 2000 (DE) ............................. 100 29 529

(51) Int. Cl.
*G02B 5/126* (2006.01)

(52) U.S. Cl. ....................................... 359/534; 359/536
(58) Field of Classification Search ................ 359/534, 359/536, 537
See application file for complete search history.

(56) References Cited

U.S. PATENT DOCUMENTS

| 3,025,764 | A | | 3/1962 | McKenzie et al. |
| 3,700,305 | A | | 10/1972 | Bingham |
| 3,781,083 | A | | 12/1973 | Eigenmann |
| 4,848,882 | A | * | 7/1989 | Suzuki et al. ............ 359/652 |
| 6,351,659 | B1 | * | 2/2002 | Vilsmeier ............... 600/407 |

FOREIGN PATENT DOCUMENTS

| DE | 19639615 | 4/1998 |
| WO | WO 97/23423 | 7/1997 |
| WO | WO 99/27839 | 10/1999 |

* cited by examiner

Primary Examiner—Euncha P. Cherry
(74) Attorney, Agent, or Firm—Fish & Richardson P.C.

(57) ABSTRACT

The invention relates to a reflector system for positioning a medical instrument or of body parts of a patient or for any determination of position, which is characterized by reflectors (3, 4, 5) that are configured as transparent retroreflective spheres and may consist of a material with a refractive index of preferably 1.9.

15 Claims, 2 Drawing Sheets

REFLECTOR SYSTEM FOR DETERMINING POSITION

BACKGROUND OF THE INVENTION

The invention concerns a reflector system for determining position, as set forth in the classifying portion of claim 1.

The optical navigational systems which are known per se from the state of the art use either active optical marks or passive marks, for determining position. Generally light emitting diodes (LEDs) are used as the active marks. The passive marks are usually balls with a reflective coating or retroreflective foils.

DE 196 39 615 C2 discloses a so-called reflector referencing system for surgical and medical instruments, which is formed from a radiation source and a reflector assembly having at least two reflectors. That reflector system provides a marker system for effecting determination of the position of parts of the body or instruments. Surgical instruments for example can be fitted with a three-reflector adaptor which delivers a reflection image which is characteristic of that instrument. In determining the position of parts of the body to be treated each landmark delivers an image which is characteristic only in respect of itself, both in terms of diagnostic patient data acquisition and also in terms of subsequent treatment monitoring. The reflectors are in the form of balls and are provided with a reflective coating. Such balls produce a uniform reflection image, when considered from all directions in space.

The passive marks which are fitted to devices and instruments in medical engineering have to be frequently disinfected and sterilized. Sterilization of the medical instruments can be effected for example by means of gas sterilization or steam sterilization which can take up to a full working day, which means that with frequent use several sets of instruments have to be purchased. It is only in that way that it is possible to guarantee that sterilized instruments are available at any time.

Therefore, in order to achieve a reduction in complication and costs, DE 196 39 615 C2, proposed that the very expensive marks are interchangeably fitted to the medical devices and instruments. For that purpose the marks are fitted in the form of passive reflectors to an adaptor which in turn is releasably connected to the instrument. That now admittedly means that the marks are interchangeable. The fundamental problem however is not eliminated. For, the known passive marks withstand the cleaning procedures only a few times and have to replaced by fresh marks after just a relatively few uses.

SUMMARY OF THE INVENTION

Based on the above-indicated state of the art, the object of the present invention is to produce a reflector system of the kind set forth in the opening part of this specification, involving the use of passive marks which reflect over a wide angular range and which can withstand a multiplicity of the cleaning procedures which are possible hitherto, and can be autoclaved virtually as often as may be desired. It will be appreciated in that respect that the medical demands also have to be met.

In accordance with the invention that object is attained by the features of claim 1. Advantageous configurations and developments of the invention are described in the appendant claims.

The invention is based on the realization that the known reflective coatings on balls or other geometrical mark bodies have only a limited service life. That disadvantage is completely eliminated with the present invention insofar as, in accordance with the invention, a transparent ball is used as a passive mark, which ball has a refractive index which can be selected in dependence on the desired angle of beam spread of a light beam and thus acts as a reflector in the UV-range, in the visible range and in the infrared range (IR). In that respect the front surface of the ball, on which the incident beams impinge, acts as a lens, with the focal point being on the rear surface of the ball.

The reflector system according to the invention makes use of reflection at the transition of materials of different optical densities, which corresponds to a respective different refractive index. As there is no preferential direction in the case of the transparent ball of such a nature, the ball provides for retroreflection in any angle in space. As a result for example with a refractive index of 1.9±0.1, for glass, light beams near the axis are reflected in the same direction. In contrast the light beams which are remote from the axis are reflected at a given angle in space. By changing the refractive index it is possible to alter and appropriately maximize the light output which is reflected at a given angle in space.

In an embodiment of the invention the surface of the transparent ball can be entirely or partially part-transmissively mirror-coated or metalized. The greatest reflected intensity of the light beams is achieved at a transmission of 67% or a reflection of 33%. As an alternative thereto a predetermined angular segment of the reflector is completely metalized. As a result, a light beam is admittedly no longer reflected in all directions in space, but the reflected intensity is substantially greater than in the case of part-transmissive metalization.

In order to achieve more uniform distribution of the reflected light the metalized surfaces of the reflectors can preferably be of a diffusively reflective nature.

A particular configuration of the invention is achieved if arranged between the ball and the reflection layer (metalization) is a layer of a transparent material with a different refractive index. The angle of beam spread of the reflected light can then be influenced by the refractive index of the ball, by the refractive index of the intermediate layer used and by the thickness of the intermediate layer.

Preferably the reflector system according to the invention is employed in medical engineering for determining a position of a medical instrument or device or for determining parts of the body of patients.

BRIEF DESCRIPTION OF THE DRAWINGS

An example of the invention is illustrated in the drawing in which.

DETAILED DESCRIPTION

In quite general terms the man skilled in the art understands by reflection in physics the phenomenon that particles or waves, for example sound or light, are thrown back at interfaces, such as for example air and glass. With a very smooth interface, the law of reflection then applies, which states that the angle of incidence of the light beam is equal to the angle of reflection. The incident beam, the reflected beam and the normal of incidence lie in one plane. Regular reflection of that kind is experienced by a light beam at a mirror or a metalized surface of a body. If the surface roughnesses are greater than the wavelength of the beams, then so-called diffuse reflection occurs, in which the beams are reflected in all directions in space.

In most cases only a part of the incident radiation is reflected while the other part is absorbed or refracted. At the transition from an optically denser medium to a thinner medium, for example from glass to air or conversely from air to glass, only a part of the incident radiation is reflected while the other part is refracted. In principle the magnitude of reflection is dependent on the difference in refractive index of the two materials, in particular here glass. The light does not continue to go in a straight line but is refracted at the surface in accordance with the optical law of refraction in dependence on refractive indices.

Figure 1:
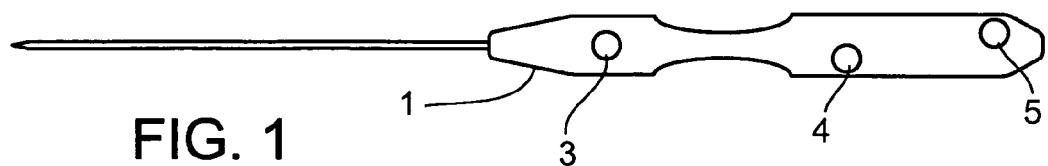
FIG. 1 is a diagrammatic view of a medical instrument for neurosurgery with passive reflectors.

The medical instrument shown in FIG. 1 represents a pointer instrument for neurosurgical interventions. The medical instrument 1 preferably operates in a cable-less manner and has a total of three passive reflectors 3, 4 and 5. It will be appreciated that more or fewer than three reflectors and other arrangements are also possible.

Figure 2:
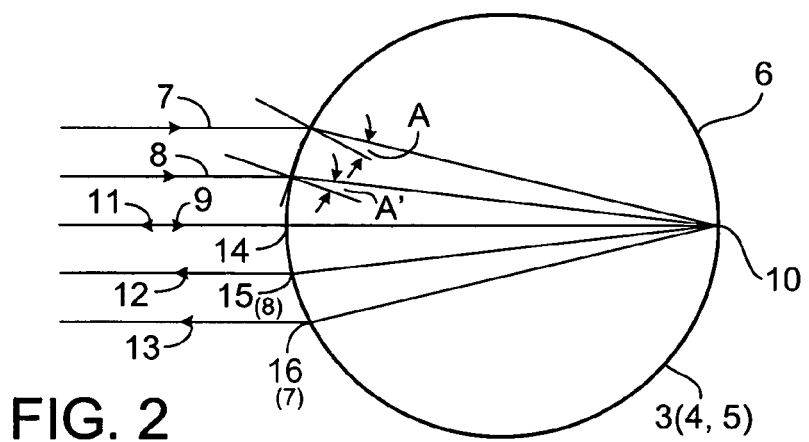
FIG. 2 shows a retroreflective ball with a refractive index of about 1.9.
Figure 3:
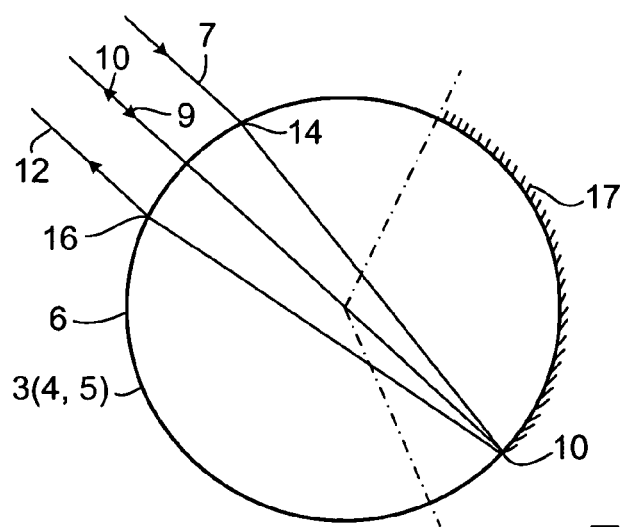
FIG. 3 shows a retroreflective ball with a partly metalized surface.
Figure 4:
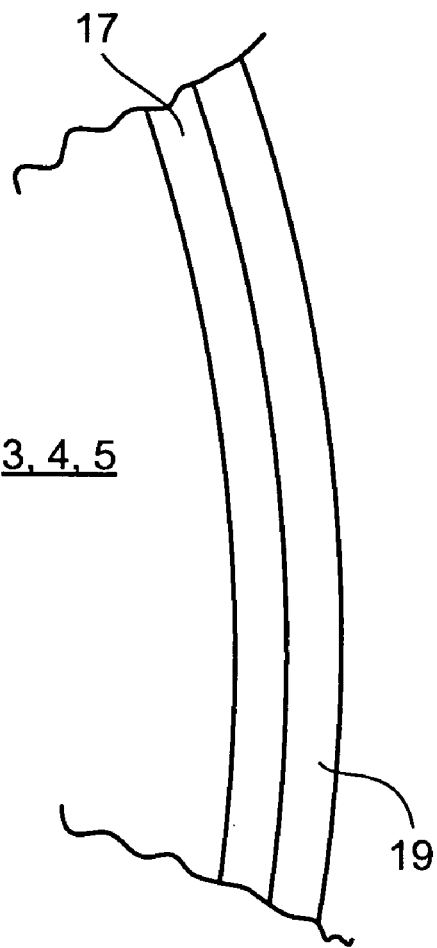
FIG. 4 shows a portion of retroreflective ball with a transparent layer.

The reflectors 3, 4 and 5 are transparent balls which have a retroreflection action, as shown in FIGS. 2 and 3. Glass preferably serves as the material for the ball. Electromagnetic radiation, generally a light beam, impinges on the surface 6 of the ball and is refracted at the interface which exists between the outside air and the ball consisting of the material glass. The air has a refractive index of 1 while high-refraction glass has a refractive index of nearly 2. The light beam passes into the ball 3, 4 and 5 as indicated by the arrows 7, 8 and 9. In this case the ball surface 6 acts like a convergent lens. The light beams 7 and 8 impinge on the surface of the ball and are deflected at an angle A and A' respectively and are passed onto the common end point 10 in the ball. The light beam 9 which is near the axis extends in a straight line after passing into the ball onto the end point 10. At that end point a part of the light beam is reflected and is reflected back again as indicated by the arrows 11, 12 and 13 and issues from the surface of the ball at an angle. In the case of a mirror surface for the ball the angle of incidence is equal or almost equal to the angle of reflection. The reflected light leaves the ball again, in which case the surface of the ball now again acts as a convergent lens.

In the example in FIG. 2 the ball (reflector 3, 4, 5) comprises glass and has no coatings or mirror or metalization layers. This means that a part of the light beams which are incident into the ball issue from the ball at the end point 10. Another and generally smaller part of the light beams 7, 8 and 9 is reflected and issues from the ball again at the reflected locations 14, 15 and 16. Those reflected light beams which issue from the ball (reflector 3, 4, 5) are recorded by a receiver system, for example a camera system, and suitably used. As the ball as shown in FIG. 2 is not metalized at any location, light beams can impinge on the surface of the ball from all angles in space and be retroreflected. The angle of beam spread for the light beams, which is associated with the transmitter, is relatively great. It is essential with this kind of reflector design that the light beams issuing after reflection from the reflectors 3, 4 and 5 are so intensive that they are reliably received by the receiver.

In the embodiment shown in FIG. 3 a given angular segment 17 of the surface of the ball of the reflector 3, 4 and 5 is metalized. That measure provides that the light beams can only pass into the ball at a given angle and be reflected there. Instead of the metalization in the angular segment 17, a diffusively scattering surface can also be envisaged. Although with this embodiment light is no longer reflected in all directions in space, the advantage of this structure is the higher level of intensity of the issuing light beams. If the ball has a diffusively scattering surface, that affords more uniform distribution of the reflected light.

It will be appreciated that the non-metalized portion of the surface of the ball can be dereflected.

The principle of retroreflection can moreover also be simulated with a lens and a concave mirror. If the focal length of the concave mirror is f, then the value 2f approximately applies in regard to the distance from the lens to the concave mirror and 2f also applies in regard to the focal length of the lens. By varying the distance or by varying the focal length of the lens it is possible to influence the angle of beam spread. A Fresnel lens can also be used in the above-indicated example.

The reflectors 3, 4 and 5 are basically subject to the physical law of refraction. More specifically, if a light beam passes from an optically thinner medium, in this case air, into an optically denser medium, in this case glass, the light beam is subjected to refraction, with the law of refraction known from physics applying.

It is expressly emphasized that these novel reflectors can be used generally and in many different ways in technology and the depicted use in medical engineering only represents a preferred area of use.

The invention claimed is:

1. A reflector system for determining position comprising:
   a passive reflector in the form of a transparent ball having a selectable uniform refractive index that is dependent on the desired angle of beam spread of a light beam; and
   a receiver device adapted and positioned to receive the light beam reflected from the passive reflector and to determine the position of the passive reflector.

2. The reflector system of claim 1 wherein the passive reflector is formed from a material that is only transparent within a specific wavelength range.

3. The reflector system of claim 1 wherein at least a portion of the surface of the transparent ball is covered with a partially-transmissive metallic layer.

4. The reflector system of claim 3 wherein the portion of the surface of the transparent ball that is covered with a partially-transmissive metallic layer is an angular segment having a predetermined size.

5. The reflector system of claim 3 wherein the passive reflector has a refractive index between 1.8 and 2.0.

6. The reflector system of claim 3 wherein the passive reflector is formed from a material that is only transparent within a specific wavelength range.

7. The reflector system of claim 3 wherein the partially-transmissive metallic layer is a diffusively reflective layer.

8. The reflector system of claim 3 further comprising a transparent layer disposed between the surface of the transparent ball and the partially-transmissive metallic layer, wherein the transparent layer has a different refractive index than the passive reflectors.

9. The reflector system of claim 1 further comprising an instrument, the passive reflector positioned on an instrument, the receiver positioned to receive the light beam and determine the position of the instrument.

10. The reflector system of claim 9 wherein the instrument is a medical instrument.

11. The reflector system of claim 9 comprising a plurality of passive reflectors, each positioned on the instrument and spaced from other passive reflectors to provide a reflection image characteristic of the instrument.

12. The reflector system of claim 1 wherein the receiver is a camera.

13. The reflector system of claim 5 wherein the refractive index is 1.9.

14. The reflector system of claim 1 wherein the passive reflector is in the form a second transparent ball within the first-mentioned transparent ball, the second transparent ball having a refractive index different than the selectable refractive index of the first-mentioned transparent ball.

15. A method of comprising:
positioning a plurality of passive reflectors in a predetermined spaced relationship on an object, each of the passive reflectors arranged to form a transparent ball having a selectable refractive index that is dependant on the desired angle of beam spread of a light beam;
illuminating at least some of the plurality of passive reflectors with light; and
detecting reflected light from illuminated ones of the passive reflectors;
determining the position of the object based on the characteristics of the reflected light from the illuminated ones of the passive reflectors.

* * * * *